(12) United States Patent
Carvell et al.

(10) Patent No.: US 10,058,352 B2
(45) Date of Patent: Aug. 28, 2018

(54) METHODS AND DEVICES SUITABLE FOR IMPROVED REATTACHMENT OF DETACHED CARTILAGE TO SUBCHONDRAL BONE

(71) Applicant: Smith & Nephew, Inc., Memphis, TN (US)

(72) Inventors: Kelsey Jean Carvell, Malden, MA (US); Ruth Cheng, Natick, MA (US); Graham Smith, Newburyport, MA (US); Drew Burdon, North Yorkshire (GB); Paul Alexander Torrie, Marblehead, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 14/075,150

(22) Filed: Nov. 8, 2013

(65) Prior Publication Data
US 2014/0147433 A1   May 29, 2014

Related U.S. Application Data

(60) Provisional application No. 61/736,661, filed on Dec. 13, 2012, provisional application No. 61/723,973, filed on Nov. 8, 2012.

(51) Int. Cl.
| | | |
|---|---|---|
| *A61K 31/19* | (2006.01) | |
| *A61M 1/00* | (2006.01) | |
| *A61B 17/16* | (2006.01) | |
| *A61K 36/752* | (2006.01) | |
| *A61K 38/48* | (2006.01) | |
| *A61B 17/56* | (2006.01) | |

(52) U.S. Cl.
CPC .......... *A61B 17/56* (2013.01); *A61B 17/1604* (2013.01); *A61B 17/1606* (2013.01); *A61K 31/19* (2013.01); *A61M 1/0023* (2013.01); *A61M 1/0058* (2013.01); *A61B 2017/564* (2013.01); *A61K 36/752* (2013.01); *A61K 38/4873* (2013.01); *A61M 2210/02* (2013.01); *A61M 2210/08* (2013.01)

(58) Field of Classification Search
None
See application file for complete search history.

(56) References Cited

U.S. PATENT DOCUMENTS

| | | | |
|---|---|---|---|
| 4,542,025 A | 9/1985 | Tice et al. | |
| 4,827,911 A | 5/1989 | Broadwin et al. | |
| 4,842,578 A | 6/1989 | Johnson et al. | |
| 5,206,023 A | 4/1993 | Hunziker | |
| 5,433,215 A | 7/1995 | Athanasiou et al. | |
| 5,871,462 A | 2/1999 | Yoder et al. | |
| 5,906,934 A | 5/1999 | Grande et al. | |
| 5,944,686 A * | 8/1999 | Patterson | A61B 17/3203 604/22 |
| 6,068,604 A | 5/2000 | Krause et al. | |
| 6,491,692 B1 | 12/2002 | Meislin | |
| 6,784,282 B2 | 8/2004 | Hwang et al. | |
| 7,575,743 B2 | 8/2009 | Hunziker | |
| 7,727,542 B2 | 6/2010 | DiBenedetto et al. | |
| 7,780,740 B2 | 8/2010 | Steinberg | |
| 2001/0037106 A1 | 11/2001 | Shadduck | |
| 2002/0091403 A1 | 7/2002 | Bonutti | |
| 2002/0116063 A1 | 8/2002 | Giannetti et al. | |
| 2002/0122790 A1 | 9/2002 | Hunziker | |
| 2003/0008826 A1 | 1/2003 | Hwang et al. | |
| 2003/0009166 A1 | 1/2003 | Moutafis et al. | |
| 2003/0040763 A1 | 2/2003 | Moutafis et al. | |
| 2003/0099630 A1 | 5/2003 | DiBenedetto et al. | |
| 2003/0114936 A1 | 6/2003 | Sherwood et al. | |
| 2003/0125660 A1 | 7/2003 | Moutafis et al. | |
| 2003/0125727 A1 | 7/2003 | Truckai et al. | |
| 2003/0207232 A1* | 11/2003 | Todd | A61C 1/0092 433/88 |
| 2004/0033212 A1 | 2/2004 | Thomson et al. | |
| 2004/0092921 A1 | 5/2004 | Kadziauskas et al. | |
| 2004/0214322 A1 | 10/2004 | Park et al. | |
| 2005/0043814 A1 | 2/2005 | Kusanagi et al. | |
| 2006/0083728 A1 | 4/2006 | Kusanagi et al. | |
| 2006/0156875 A1 | 7/2006 | McRury et al. | |

(Continued)

FOREIGN PATENT DOCUMENTS

| | | |
|---|---|---|
| CN | 101352581 A | 1/2009 |
| EP | 2389881 A1 | 11/2011 |
| GB | 2093353 A | 9/1982 |
| WO | 2000002905 | 1/2000 |
| WO | 2005023324 A1 | 3/2005 |
| WO | 2008086147 A1 | 7/2008 |
| WO | 2010148125 A1 | 12/2010 |
| WO | 2011089779 A1 | 7/2011 |

OTHER PUBLICATIONS

Mithoefer, Kai, et al. "Chondral resurfacing of articular cartilage defects in the knee with the microfracture technique." JBJS Essential Surgical Techniques 1 suppl 2 (2006): 294-304.*

(Continued)

*Primary Examiner* — John Pak
*Assistant Examiner* — Daniel L Branson
(74) *Attorney, Agent, or Firm* — Burns & Levinson, LLP; Joseph M. Maraia (57) ABSTRACT

The methods and devices disclosed herein are effective in the promoting the reattachment of delaminated cartilage to bone. The methods (and related devices) are effective in the removal of the acellular layer of the delaminated cartilage or effective in the indentation of the acellular layer of the delaminated cartilage thereby exposing the underlying chondrocyte cells and thereby allowing the promotion of the reattachment of the delaminated cartilage.

19 Claims, 7 Drawing Sheets

(56) References Cited

U.S. PATENT DOCUMENTS

| | | | |
|---|---|---|---|
| 2006/0229550 | A1 | 10/2006 | Staid et al. |
| 2007/0083120 | A1 | 4/2007 | Cain et al. |
| 2007/0088217 | A1 | 4/2007 | Babaev |
| 2007/0098675 | A1 | 5/2007 | Elisseeff et al. |
| 2007/0179343 | A1 | 8/2007 | Shelokov |
| 2008/0044423 | A1 | 2/2008 | Cochrane et al. |
| 2008/0199513 | A1* | 8/2008 | Beretta ............ A61B 17/00491 424/443 |
| 2008/0311190 | A1 | 12/2008 | Chtourou |
| 2009/0047322 | A1 | 2/2009 | Vange et al. |
| 2009/0155378 | A1 | 6/2009 | Behnam et al. |
| 2009/0221076 | A1 | 9/2009 | Kato et al. |
| 2010/0036503 | A1 | 2/2010 | Chen et al. |
| 2010/0166894 | A1 | 7/2010 | Tai |
| 2010/0211173 | A1 | 8/2010 | Bardos et al. |
| 2010/0217268 | A1 | 8/2010 | Bloebaum et al. |
| 2010/0247651 | A1 | 9/2010 | Kestler et al. |
| 2010/0297066 | A1 | 11/2010 | Stopek et al. |
| 2011/0086008 | A1 | 4/2011 | Hoemann et al. |
| 2012/0014884 | A1 | 1/2012 | Trivedi et al. |
| 2012/0053606 | A1 | 3/2012 | Schmitz et al. |
| 2012/0107412 | A1 | 5/2012 | Gammelsaeter et al. |
| 2012/0165848 | A1* | 6/2012 | Slayton ................... A61N 7/02 606/169 |
| 2012/0265204 | A1 | 10/2012 | Schmierer et al. |

OTHER PUBLICATIONS

O'Daly, Brendan J., et al. "High power, low frequency ultrasound: meniscal tissue interaction and ablation characteristics." Ultrasound in medicine & biology 37.4 (2011): 556-567.*

Spahn, Gunter, Rosemarie Fröber, and Werner Linß. "Treatment of chondral defects by hydro jet. Results of a preliminary scanning electron microscopic evaluation." Archives of orthopaedic and trauma surgery 126.4 (2006): 223-227.*

Gaertner, Wolfgang. "Frequency dependence of ultrasonic cavitation." The Journal of the Acoustical Society of America 26.6 (1954): 977-980.*

Stafford, G.H., Bunn, J.R. and Villar, R.N., 2011. Arthroscopic repair of delaminated acetabular articular cartilage using fibrin adhesive. Results at one to three years. Hip International, 21(6).*

International Preliminary Report on Patentability dated May 21, 2015 for PCT/US2013/089123, filed on Nov. 8, 2013, 12 pages.

Goldring, M.B. "Osteoarthritis and cartilage: the role of cytokines." Current Rheumatology Reports, vol. 2, No. 6 (2000): 459-465.

Mithoefer, K. et al. Chondral Resurfacing of Articular Cartilage Defects in the Knee With the Microfracture Technique. Surgical Technique. Journal of Bone and and Joint Surgery. Sep. 1, 2006; vol. 8A, No. 1 (Supp. 2); p. 294, col. 2, lines 1-3, 10-12; p. 296, col. 1, lines 34-40; col. 2, figure 2-B; p. 297, col. 2, lines 2-5; col. 3, lines 1-6; p. 298, figure 4-B.

Frisbie, DD et al. Effects of Calcified Cartilage on Healing of Chondral Defects Treated With Microfracture in Horses. American Journal of Sports Medicine. Jul. 10, 2006; vol. 34, No. 11, p. 1825, col. 2, lines 53-58.

Gruber, J et al. Induction of Interleukin-1 in Articular Cartilage by Explantation and Cutting. Arthritis and Rheumatism. Aug. 2004; vol. 50, No. 8, p. 2539, col. 1, lines 1-29.

Hunziker, EB et al. Removal of Proteoglycans From the Surface of Defects in Articular Cartilage Transiently Enhances Coverage by Repair Cells. Journal of Bone and Joint Surgery. Jan. 1998; vol. 80, No. 1, p. 145, col. 1, lines 16-22; p. 145, figure 1; p. 146, col. 1, lines 1-2.

International Search Report dated Apr. 8, 2014 for PCT/US2013/69123, filed on Nov. 8, 2013, 17 pages.

Saw, et al., "Articular Cartilage Regeneration with Autologous Peripheral Blood Progenitor Cells and Hyaluronic Acid After Arthroscopic Subchondral Drilling: A Report of 5 Cases with Histology", the Journal of Arthroscopic and Related Surgeries; vol. 27, No. 4; Apr. 2011; pp. 493-605.

* cited by examiner

METHODS AND DEVICES SUITABLE FOR IMPROVED REATTACHMENT OF DETACHED CARTILAGE TO SUBCHONDRAL BONE

BACKGROUND

Over 16 million people in the U.S. suffer from severe joint pain and related dysfunction, such as loss of motion, as a result of injury or osteoarthritis. In particular, loss of function of the knees and other joints can severely impact mobility and thus the patient's quality of life. The biological basis of joint problems is the deterioration of articular cartilage, which covers the bone at the joint surface and performs many complex functions. The deterioration of articular cartilage is often preceded by the delamination of the cartilage. Medical intervention at the delamination stage of the disease provides an opportunity to circumvent further degradation and associated complications.

The interface between bone and cartilage is the interface between a vascularized (the bone) and mostly avascular (the cartilage) tissue as well as mineralized (ossified) and non-minerilized collagen matrices. Traumatic injury, as well as such conditions as osteoarthritis and aging, often results in damage to the articular cartilage, which may also involve damage to the underlying bone. Often, this damage manifests itself in the delamination of the cartilage from the bone. Therefore, there is a need for a method of treatment which meets the disparate needs of both tissue types and allows or encourages the healing process to progress towards restoration of both types of tissues at the same site by promoting the reattachment of the cartilage to the bone.

Prior art methods for promoting the relamination or reattachment of cartilage to the bone are not without problems. Prior art treatments include, for example, autograph procedures such as osteochondral autograph transfer system (Mosaicplasty). These procedures remove an osteochondral plug from a non-load bearing area and graft it into the defect site. However, these procedures require invasive surgical procedures and, therefore, longer recuperative times.

Arthroscopic lavage is a "cleaning up" procedure of the knee joint. This short term solution is not considered an articular cartilage repair procedure but rather a treatment to reduce pain, mechanical restriction and inflammation. Lavage focuses on removing degenerative articular cartilage flaps and fibrous tissue. The main target group is patients with very small defects of the articular cartilage. Arthroscopic debridement is a surgical technique that is effective in removing areas of loose, mechanically redundant cartilage (joint lining) and inflamed tissue (synovitis) from the joint.

Other procedures consist of injecting cartilage cells under a periosteal flap, however, the procedure lacks inter-patient consistency with some patients maintaining little relief months or years later and the surgical procedure is technically challenging and expensive. Marrow stimulating techniques including abrasion arthroscopy, subchondral bone drilling and microfracture typically result in fibrocartilage filling the defect site. In these procedures, the subchondral bone is perforated to generate a blood clot within the defect. However, marrow stimulation techniques often insufficiently fill the chondral defect and the repair material is often fibrocartilage (which is not as good mechanically as hyaline cartilage). The blood clot takes about 8 weeks to become fibrous tissue and it takes 4 months to become fibrocartilage thus needing extensive rehabilitation time. However, there is a significant possibility of the symptoms returning as the fibrocartilage wears away, forcing the patient to undergo further articular cartilage repair.

Marrow stimulation techniques have been augmented with administration of peripheral blood monocytes (PMBCs) with limited success. Microdrilling surgery creates a blood clot scaffold on which injected PBPC's can be recruited and enhance chondrogenesis at the site of the contained lesion (Saw, K Y, et al., (Epub 2011 Feb. 19). "Articular cartilage regeneration with autologous peripheral blood progenitor cells and hyaluronic Acid after arthroscopic subchondral drilling: a report of 5 cases with histology". *Arthroscopy* 27 (4):493).

Allogenic transplantation of osteochondral grafts has had clinical success, but supply is limited and has a risk of infection. This technique/repair requires transplant sections of bone and cartilage. The damaged section of bone and cartilage is removed from the joint then a new healthy dowel of bone with its cartilage covering is punched out of the same joint and replanted into the hole left from removing the old damaged bone and cartilage. The healthy bone and cartilage are taken from areas of low stress in the joint so as to prevent weakening the joint. Depending on the severity and overall size of the damage multiple plugs or dowels may be required to adequately repair the joint, which becomes difficult for osteochondral autografts and can limit its use to non-severely damaged tissue.

The prior art techniques involving removal of the delaminated cartilage is actually not in the patient's best interest because, as described above, the tissue that forms to replace the removed cartilage, called fibrocartilage, is not as robust as the original hyaline cartilage.

Other prior art techniques include the use of scaffolds or matrixes to provide a structure upon which chondrocytes may migrate and form new cartilage. For example, one such technique is provided in US Patent Application No. 2003/0114936, which describes implantable composite materials of gradated matrices for the promotion of cell growth, which is incorporated herein by reference. Other prior art references directed towards the use of scaffolds and matrices are described, infra.

Thus, because of the limitations of the prior art procedures, it has been recognized that reattachment of the hyaline cartilage is desirable. The hyaline cartilage does not readily reattach on its own—if it did treatment options would not be necessary. Prior art attempts have used adhesives, for example. However, these attempts have met with limited success. This is at least in part because even so called "biocompatible" adhesives are made from materials foreign to the patient and/or the joint. Thus, breakdown of the adhesion frequently occurs thereby providing only a temporary solution to the condition. Further, the adhesive layer creates a barrier to the cartilage cells that are necessary for reattachment of the cartilage to the underlying bone.

Thus, what is needed in the art are devices and procedures that provide for the successful reattachment of delaminated hyaline cartilage preferably with minimal surgical intervention.

SUMMARY OF THE INVENTION

The present invention describes devices and methods for the reattachment of delaminated cartilage from the underlying bone. Delaminated cartilage acquires an acellular layer at the surface that is proximal to the bone surface. The major barrier to reattachment is the acellular layer. In essence, the acellular layer acts to prevent viable cells from attaching to the underlying subchondral bone. The invention is related to the novel and non-obvious discovery that removal or perforation of this acellular layer promotes reattachment of the delaminated cartilage to the surface of the subchondrial bone It has been identified by the inventors that more successful regrowth between the cartilage and subchondral bone occurs if a thin layer (approximately 0.1 mm=100 μM although the dimension may be from 0.02 mm to 1.0 mm depending on the particular circumstances entailed) of material is removed from the cartilage surface prior to joining. Although the inventors do not wished to be limited by theory, it is believed that removal of the acellular layer aids the reattachment of the cartilage to the subchondrial bone by exposing living chondrocytes in the cartilage to the bone surface. In other words, the present inventors found that if the acellular layer is removed, reattachment of the cartilage to the bone can commence because viable cells can, for example, form attachments with the bone surface and reestablish a healthy extracellular environment. One reason why prior art biocompatible adhesives tend to fail is because they are attempting to 'glue' dead cells to healthy tissue. The removal of the acellular tissue and dead cells should be performed gently, otherwise further layers of cells may be damaged and a new acellular layer may be created. The present invention is directed towards several devices and methods of gently removing part of or all of the acellular layer of the delaminated cartilage thereby aiding in the reattachment of the delaminated cartilage to the subchondrial bone It has also been discovered by the inventors that the perforation or indentation of the delaminated cartilage can expose chondrocytes and thereby aid in the reattachment of the delaminated cartilage to the subchondral bone. It is believed by the inventors that the controlled removal of a thin layer of cartilage (the acellular layer) or the indentation or perforation of the acellular layer has not been attempted in the art with regard to promoting the reattachment of delaminated cartilage to the underlying bone. Although the inventors do not wished to be limited by theory, it is believed that removal of the acellular layer aids the reattachment of the cartilage to the subchondral bone by exposing living chondrocytes in the cartilage to the bone surface.

Methods of causing the removal of the acellular layer of the delaminated cartilage include mechanical methods. Such mechanical methods may include, for example water pressure via a water jet, tissue suction and cavitation (e.g., ultrasonic cavitation). Further, indentations may be made in the surface of the delaminated cartilage that faces the subchondiral bone by use of specially designed rollers and pads that have "pins," "spikes" or other means for creating multiple holes or punctures (punctuate) in the surface of the delaminated cartilage sufficient to pierce the acellular layer. These devices are discussed in greater detail in the Detailed Description of the Invention, infira.

All of these embodiments may include mechanical preparation of the subchondral bone bed (e.g., microfracture, Pridie drilling, etc.). All of these embodiments may also include the administration of biocompatible adhesives, the use of which is known to one of skill in the art. Further, the procedures of the present invention may be used with exfoliation techniques described infra.

Further, all of these embodiments may include inflammation of the treatment area and said inflammation may provide further degradation of the acellular layer of the delaminated cartilage surface. Further still, exfoliants, as described below, may be used with any of the embodiments of the invention.

DESCRIPTION OF THE DRAWINGS

FIGS. 2 (A & B) shows photographs of the progression of the searing process. The shearing often starts as a bubble, as illustrated in the right hand photograph (A), and progresses into an open flap, as illustrated in the left hand photograph (B).

FIGS. 11 (A) and (B) shows embodiment of the plate or pad indenter of the present invention with a counter force plate attached.

DETAILED DESCRIPTION OF THE INVENTION

Cartilage is an avascular tissue composed of about 5-10% by weight of living cells. There are three major types of cartilage in the body: hyaline, fibrocartilage, and elastic cartilage. Hyaline cartilage covers the epiphyses of the bone and, in synovial joints, lies within a fluid filled capsule. Fibrocartilage composes the intervertebral discs separating the vertebrae of the spinal columns. Elastic cartilage is present in areas requiring extreme resilience, such as the tip of the nose. Cartilage is formed by and contains cells called chondrocytes.

Articular cartilage is composed of hyaline cartilage which has unique properties, such as viscoelastic deformation, that allow it to absorb shock, distribute loads and facilitate stable motion. Self-repair of hyaline cartilage is limited and the tissue that forms is usually a combination of hyaline and fibrocartilage, which is not as robust as the original hyaline cartilage, does not perform as well as hyaline cartilage and can degrade over time.

The extracellular matrix of hyaline cartilage contains closely packed Type II collagen fibers and proteoglycans including hyaluronate and glycoaminoglycans in a chondroitin sulfate matrix. Chondrocytes receive nutrients and dispose of wastes by diffusion through the matrix and are believed to have limited mobility or ability to divide and regenerate damaged tissue. Chondrocytes normally produce anti-angiogenesis factors. However, when large areas of cartilage are damaged, overgrowth by fibroblasts and neovascularization of the area may result in the formation of scar tissue or callus instead of articular cartilage. A subsequent ingrowth of bone forming cells may result in calcium deposition in these areas, causing further deformation of the local area.

Although attempts have been made to facilitate repair of the bone-cartilage interface in the prior art (as described above), those attempts provide the patient with a suboptimal solution to the condition often resulting in limited mobility due to stiffness and discomfort or pain. The present invention provides a greatly improved solution to the repair of delimitation of cartilage from the underlying bone thereby resulting in greatly improved patient recovery.

The prior art techniques involving removal of the delaminated cartilage is actually not in the patient's best interest since the tissue that forms to replace the removed cartilage, called fibrocartilage, is not as robust as the original hyaline cartilage. Thus, it has been recognized that reattachment of the hyaline cartilage is desirable. The hyaline cartilage does not readily reattach on its own—if it did treatment options would not be necessary.

The present invention is directed towards the inventive concept that the delaminated hyaline cartilage of the patient's joint can be induced to reattach to the underlying bone with a minimally invasive procedure. The present inventors have discovered that successful regrowth between the cartilage and subchondral bone occurs if a thin layer of material is removed from the cartilage surface (the surface facing the bone) or that layer is indented, or both, prior to joining.

Numerous devices and methods can be used to promote the removal of the thin layer of cartilage material. For example, the devices of the present invention include indenters, suction devices, cavitation devices and water jets. All of these devices have one thing in common as related to promoting the reattachment of delaminated cartilage to the subchondral bone—they provide for the exposure of cellular tissue that can mediate the reattachment of the delaminated cartilage to the bone. These devices, at least in part, promote the removal of the thin layer of cartilage material (e.g., the acellular layer) by providing fluid movement. That is, these devices provide for the exposure of cellular tissue by causing the movement of fluid (preferably, e.g., one or more of saline solutions, buffered solutions or other physiologically compatible solutions, etc.) over the surface of the delaminated cartilage thereby removing part of or all of the acellular material.

Figure 1:
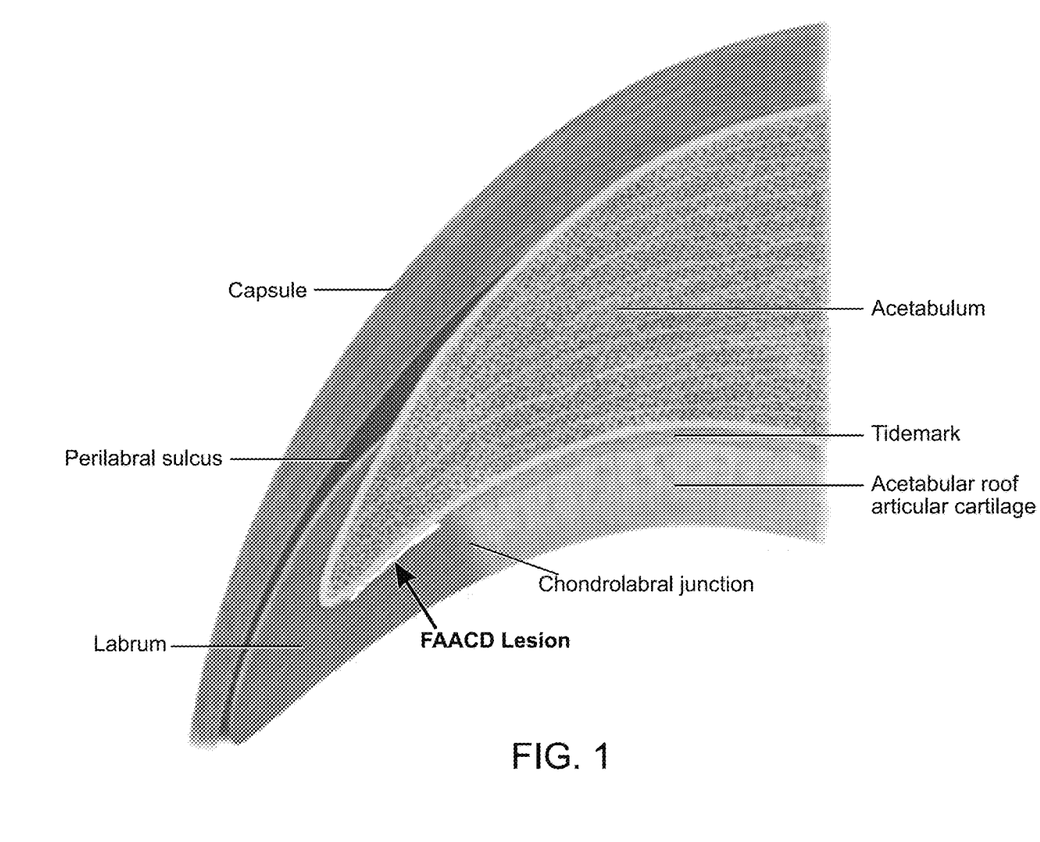
FIG. 1 shows a schematic representation of the separation of the cartilage with the underlying bone. The "tidemark," as indicated in the figure, is the cartilage-bone interface where the cartilage lining of the joints often shears off of the bone.
Figure 2:
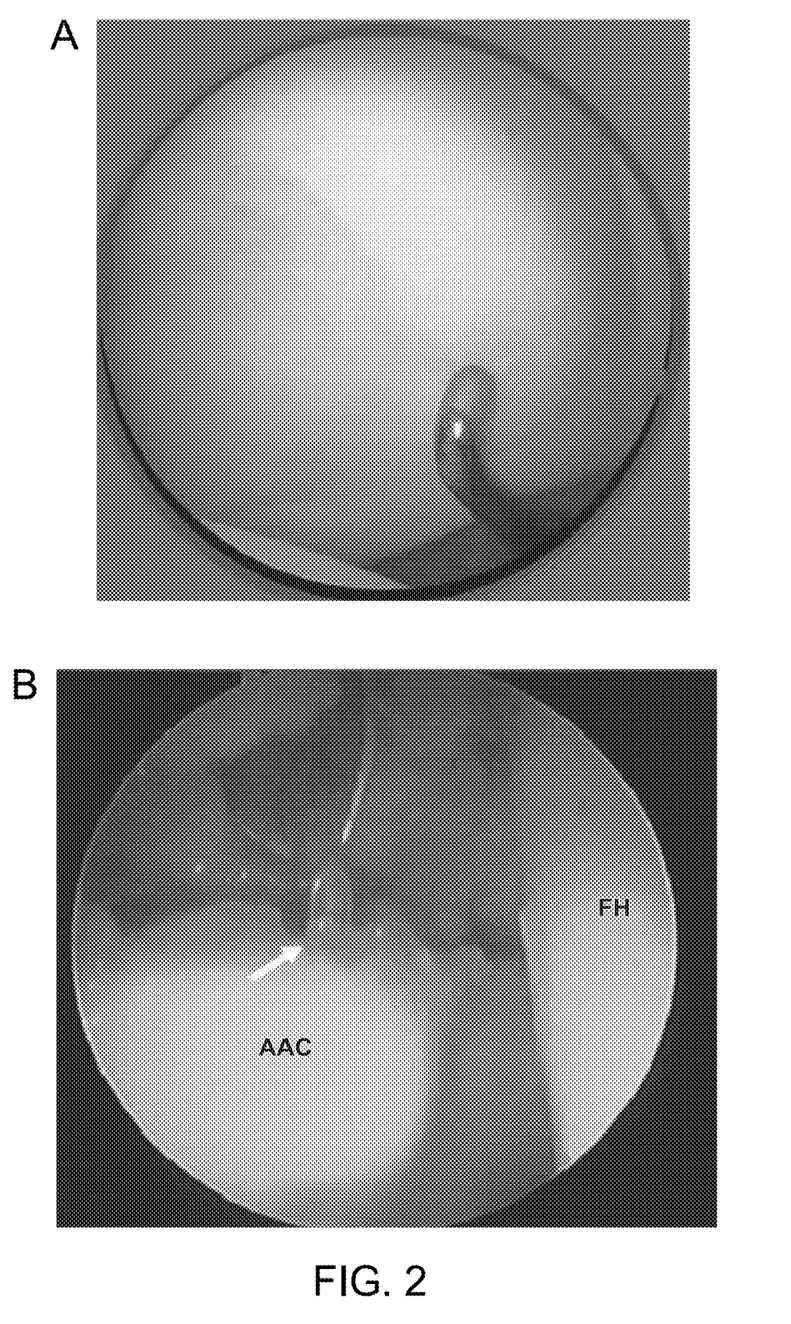
Figure 3:
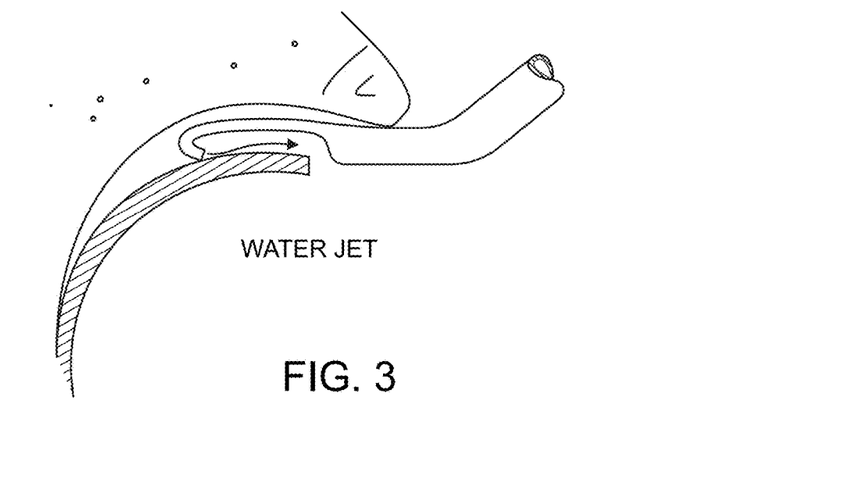
FIG. 3 shows the insertion of a water jet between the delaminated cartilage and associated subchondrial bone of a joint.
Figure 4:
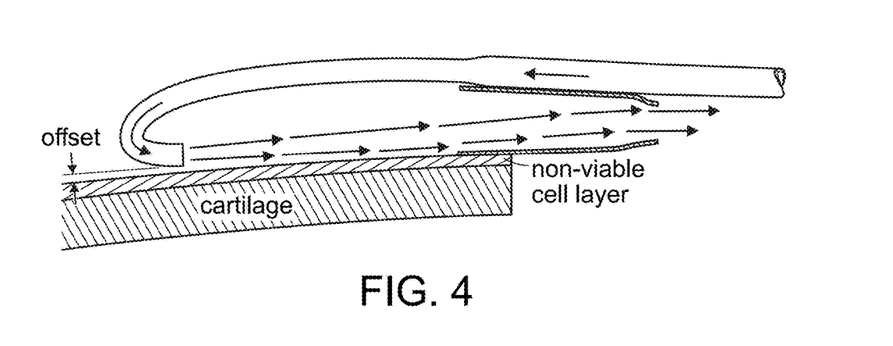
FIG. 4 shows the use of a receiving tube with the water jet of the present invention.

Exemplary devices suitable for the removal of the acellular layer of the delaminated cartilage include water jets (see, FIGS. 3 & 4) used in a procedure similar to arthroscopy. In arthroscopy the joint is usually filled with saline solution (or other suitable fluid). When a high velocity stream of fluid (for example, saline) is passed in close proximity to tissue, as exemplified by the present invention, it draws that tissue into the stream via the Bernoulli Effect. By controlling the "offset" of the stream to the tissue, the fluid pressure used and the distance of the stream from the tissue, a controlled removal of the acellular layer occurs. The flow may be distal to proximal or proximal to distal. A receiving tube can be used to control the procedure and suction can be incorporated into the receiving tube. Examples of water jets as used in the medical field are exemplified in the following documents, all of which are incorporated herein by reference: US Patent Publication Nos. 2006/0229550, US 2006/0156875, US 2003/0125660, US 2003/0009166 and U.S. Pat. No. 5,871,462.

Figure 5:
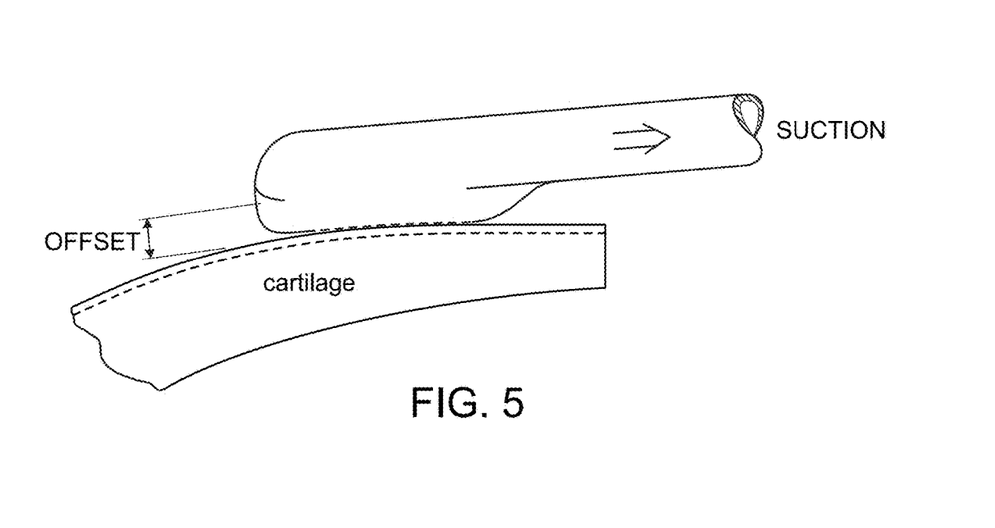
FIG. 5 shows a suction device being used to remove unwanted tissue from the surface of delaminated cartilage. The device in this figure exemplifies a fixed offset.

Tissue suction is another technique that the present inventors have found to be suitable for the removal of the acellular layer of material from the surface of the delaminated cartilage. The device of this embodiment is used, for example, arthoscopically. The device provides a gentle suction at the debonded/delaminated cartilage surface facing the subchondral bone. The gentle suction is used to remove pieces of cartilage tissue across the most or all of the cartilage area or within punctate sections of the delaminated cartilage (see, FIG. 5). The negative pressure of the suction device is regulated to be able to remove acellular and/or fibrillated material without causing additional damage to the area. In addition to suction intensity, the distance from the distal suction opening to the cartilage surface to be treated is used to control tissue removal. In one embodiment a fixed offset would be used as is shown in FIG. 5. Examples of suction devices as used in the medical field are exemplified in the following documents, all of which are incorporated herein by reference: US Patent Publication Nos. 2002/0091403, US 2010/0217268, US 2007/0179343, and U.S. Pat. No. 6,491,692, European Patent No. 2389881, PCT Patent publication No. WO 11/089779 and United Kingdom Patent No. GB 2,093,353.

Figure 6:
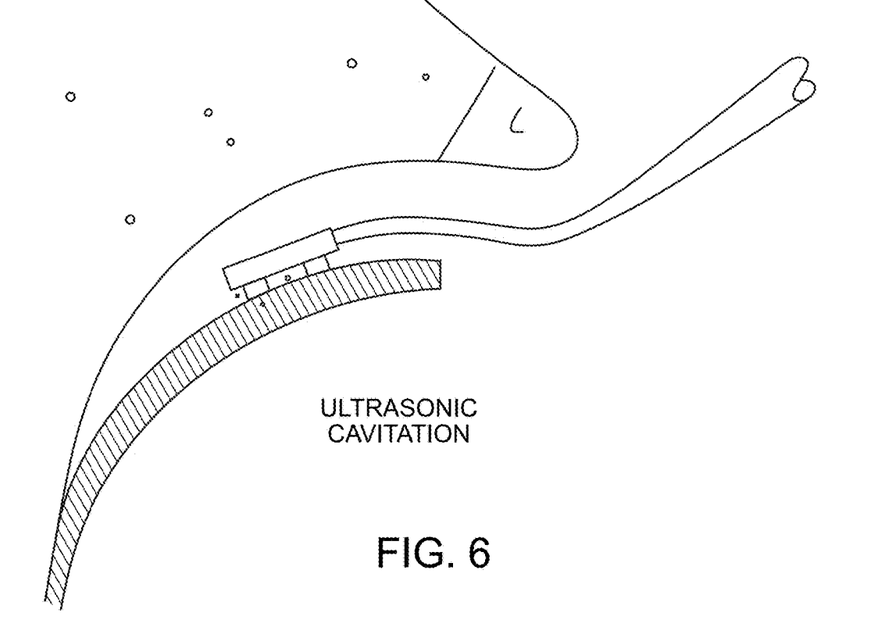
FIG. 6 shows an exemplification of the ultrasonic cavitation device of the present invention contacting the delaminated cartilage between the cartilage and the subchondrial bone.
Figure 7:
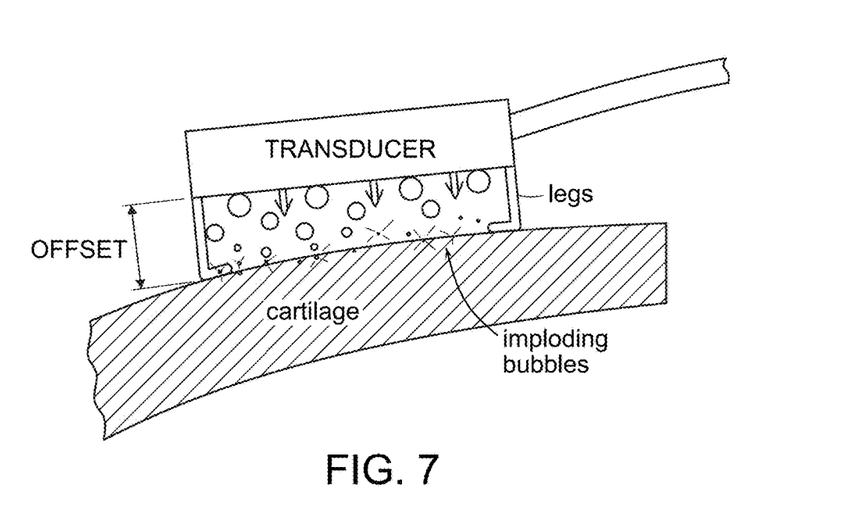
FIG. 7 shows the transducer of the cavitation device with legs designed to provide offset and to shield the arthroscopic device from visibility blocking bubbles.

Cavitation is another technique that the present inventors have contemplated to be suitable for the removal of the acellular layer of material from the surface of the delaminated cartilage. The device of this embodiment is used, for example, arthoscopically. In arthroscopy the joint is usually filled with saline solution (or other suitable fluid). When an ultrasonic transducer is introduced into this environment (see, FIG. 6) it immediately causes microscopic bubbles to travel out of the transducer. When these bubbles collapse (i.e., implode) less than 1 second later, usually in milliseconds, whatever they are on gets eroded away. By incorporating legs (see, FIG. 7) onto the transducer that have a critical offset, the bubbles can be forced to collapse on the nonviable cartilage cells (the acellular layer). Further, the degree of removal of the tissue can be controlled by regulating the current to the transducer and the power rating of the transducer. The cavitation bubbles may interfere with arthroscopic visibility thus an in some embodiments the bubbles could be contained by, for example, forming the continuous legs into a cylinder and/or, incorporating a suction device into the cavitation device. Examples of cavitation devices as used in the medical field are exemplified in the following documents, all of which are incorporated herein by reference: US Patent Publication Nos. 2001/0037106, US 2007/0083120, US 2004/0092921, US 2007/0088217, US 2003/0125727 and U.S. Pat. No. 4,827,911.

Figure 8:
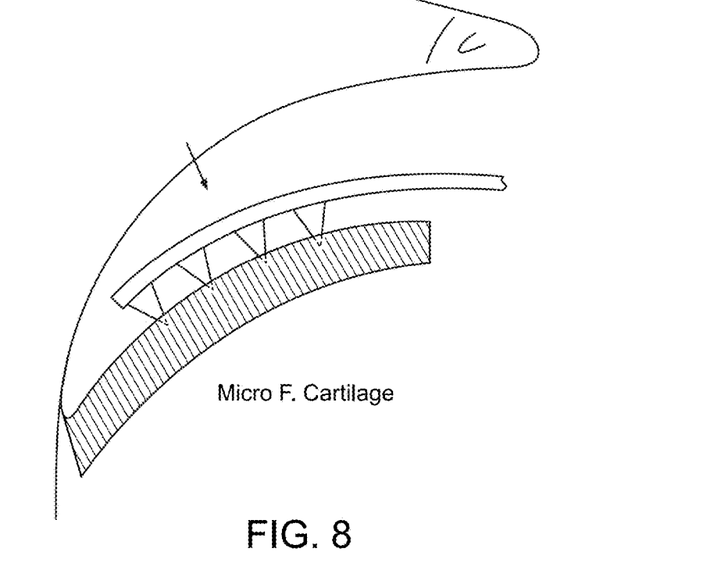
FIG. 8 shows an indentation device of the present invention placed between the delaminated cartilage and subchondral bone with the indenters push into the cartilage.
Figure 9:
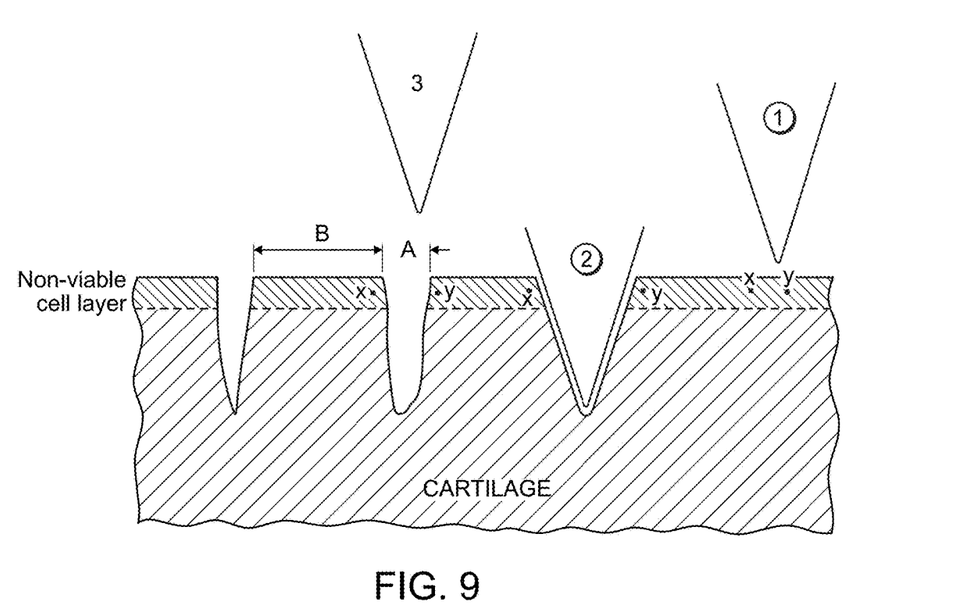
FIG. 9 shows a close-up diagram of indenters as they are used in the present invention. The enumerated indenters (1, 2 and 3) indicate a time sequence with indenter 1 prior to entry into the cartilage, indenter 2 after entry into the cartilage and indenter 3 after removal from the cartilage. The acellular layer is indicated with hash marks. Indented area is indicated as "A" and non-indented area as "B." The indenter gently separate adjacent points "X" and "Y" leaving diameter "A" without acellular tissue and/or nonviable cells.
Figure 10:
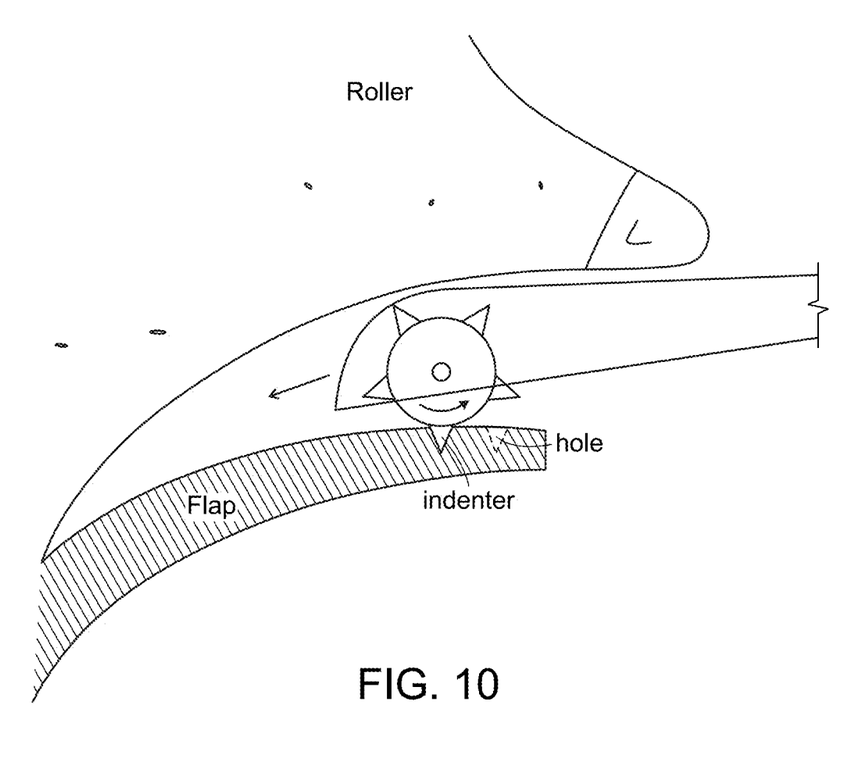
FIG. 10 shows an embodiment of the rolling indenter of the present invention.
Figure 11:
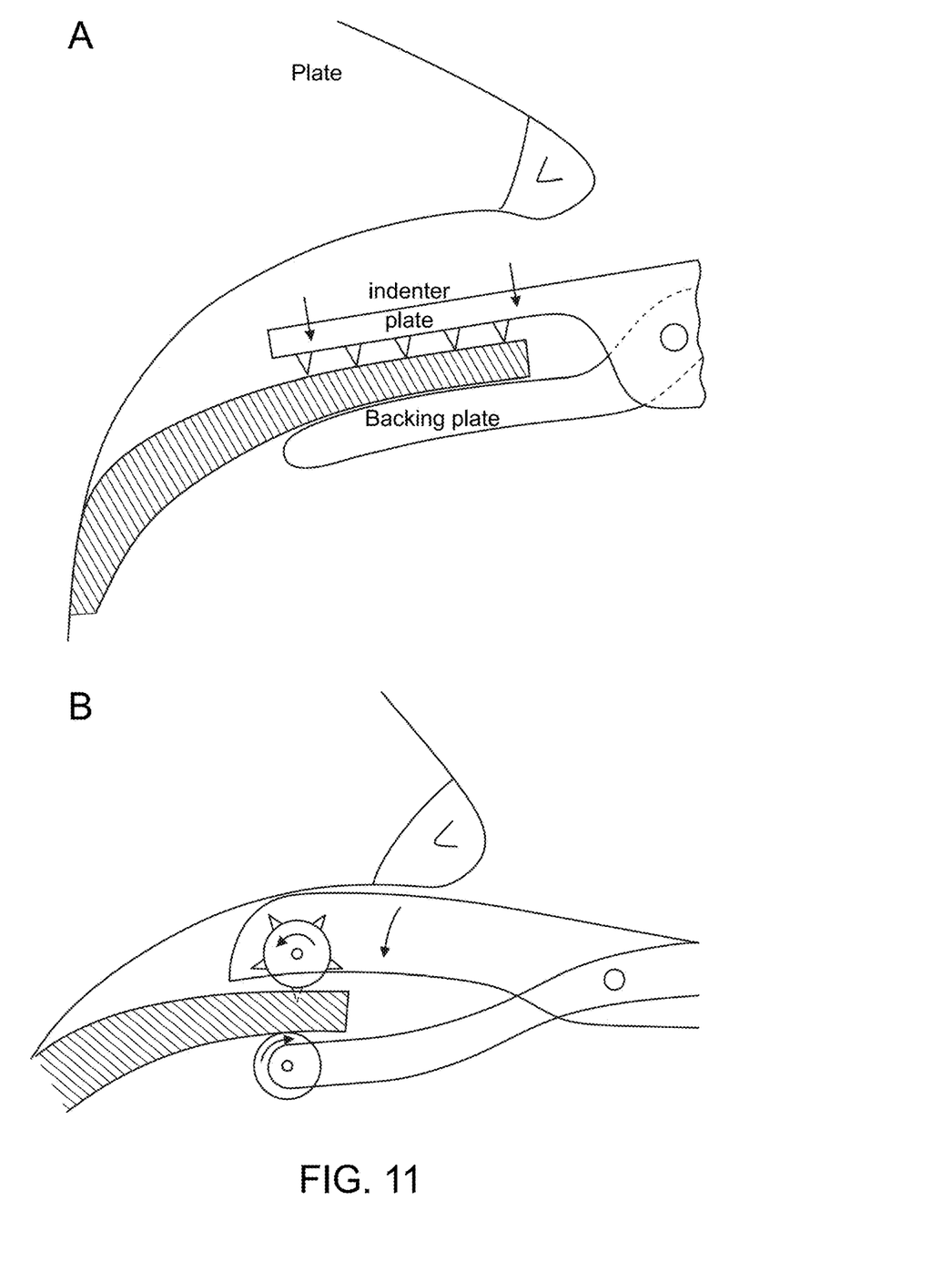

Indentation is another technique the present inventors have found to be suitable for the displacement of the acellular layer of material from the surface of the delaminated cartilage. Indenters of the present invention can be, for example, pads (see, FIGS. 8 & 9) or rollers (see, FIG. 10) containing many short mechanical pegs, spikes or the like, to gently create perforations in the cartilage. This creates "islands" or holes that aid in the reattachment of the delaminated cartilage to the subchondral bone. Since the holes are made on the cartilage, an avascular tissue, there is no blood flow. The indenters gently separate adjacent points on the surface of the cartilage, denoted "X" and "Y" in FIG. 9 leaving a hole or indentation ("A" in FIG. 9) without acellular material or nonviable cells. The intent of the invention is to have the ratio of "A" (indentations) to "B" (non indented area) be high so that the maximum number of viable cells is exposed without causing weakness of the cartilage. Indenters can be used on a roller or on a pad or plate that is pressed into the cartilage. To apply counter force to the indenters, another roller or plate is used on the outer surface of the cartilage, as exemplified in FIGS. 11A & B. Any combination of indenter (roller or plate) and backing (roller or plate) can be used. Examples of indentation devices as used in the medical field are exemplified in the following documents, all of which are incorporated herein by reference: U.S. Pat. No. 5,433,215, U.S. Pat. No. 6,068,604 and PCT Publication No. WO 10/148125.

All of these devices can be used in conjunction with biocompatible adhesives. The biocompatible adhesive may also be biodegradable, for example, over a period of days or weeks. The carrier/adhesive would aid in the reattachment of the cartilage to the underlying bone in that it would help the cartilage maintain proximity to the bone while the growth and physiological reattachment of the cartilage is promoted by the devices and methods of the present invention. Fibrin-based adhesives (e.g., fibrin glues) are a non-limiting example of a suitable carrier/adhesive.

As is known in the art, fibrin glue (also called fibrin sealant), consists of two main components: fibrinogen and thrombin. These are typically, for example, loaded into two syringes with tips forming a common port. When injected, the two components meet in equal volumes at the point of delivery. The thrombin converts the fibrinogen to fibrin by enzymatic action at a rate determined by the concentration of thrombin. The more concentrated thrombin solution produces a fibrin clot in about 10 seconds, and the more dilute thrombin solution forms the clot about 60 seconds after the glue is applied to the surgical field. Both the extrinsic and the intrinsic mechanisms of blood coagulation are bypassed, but the physiological final common pathway of coagulation is faithfully replicated. Factor XIII (present in the fibrinogen component of the glue) cross links and stabilizes the clot's fibrin monomers. Some preparations of fibrin glue contain aprotinin to delay the fibrinolytic action of plasmin. (Fibrin Glue, BMJ, 9 Apr. 1994:308:933). Fibrin glue is used as a tissue adhesive. This glue can be used for repairing dura tears, bronchial fistulas and for achieving hemostasis after spleen and liver trauma. It is also employed in "no sutures" corneal transplantation. Other biocompatible and biodegradable adhesives are known to one of ordinary skill in the art.

Examples of fibrin-based adhesives include, U.S. Patent Publication No. 2008/0831190 to Chtourou that teaches a thrombin-free, fibrinogen-based biological adhesive for therapeutic use that comprises factor VIla and a source of calcium ions suitable for use with cartilage and bone. Chinese patent application No. 101352581 (abstract only) describes compositions and methods for the repair of articular cartilage, the composition comprising fibrinogen and thrombin as a coagulation. The patents and patent publications discussed above are incorporated herein by reference.

Exfoliation is another method contemplated by and compatible with the present invention for use in the reattachment of delaminated cartilage from the underlying bone. An exfoliant is used to slough away (e.g., gently slough away) dead cells and tissues that are still adhered to viable, healthy cells and cell layers. Exfoliants are often used for dermal applications to remove dead cells and allow a better transfer of a skin care product to the healthy skin. The same concept has been adapted herein for cartilage repair. To enable the transfer of live cells for integration, the dead cells and associated tissues are removed gently. Contemplated exfoliants suitable for use in the present invention include, but are not limited to, mechanical exfoliants such as granules (or other mild abrasive) to "scrub" or otherwise remove away the dead cartilage cells. Some non-limiting examples of mechanical exfoliants contemplated by the present invention are sodium tetraborate decahydrate granules, polyethylene silica, calcium carbonate, natural ground seed or beans, aluminum oxide, monosaccharides, disaccharides, ice crystals, etc. Also contemplated by the present invention are chemical exfoliants such as, but not limited to, alpha hydroxyl acid, citrus juices, beta hydroxyl acid and papain, a natural digestive enzyme found in papya.

In some embodiments of the present invention it is contemplated that the bone surface is to be prepared in addition to the surface of the cartilage. The methods suitable to prepare the bone surface include, but are not limited to, the removal of any calcified cartilage that is adhered to the bone. The depth of the tissue removal is contemplated to be between 0.1 mm and 3.0 mm. Additionally, subchondral disruption methods such as microfracture, Pridie drilling (named after Kenneth Pridie, a British athlete and orthopedic surgeon: Pridie is known for a particular cartilage repair technique where repair by fibrocartilage formation is stimulated by drilling small holes into the subchondral bone plate after surgical debridement of cartilage defects, known as the Pridie Drilling), etc., could be performed in combination with any embodiment of the present invention.

In the context of the present invention the term "acellular cartilage layer" (and similar) refers to the layer of cartilage where few or no living (viable) chondrocytes are present at or in close proximity to the delaminated surface of the cartilage or directly exposed to the outer surface or proximal environment of the delaminated surface of the cartilage. The acellular layer typically has from 10% to 100% fewer living (viable) cells than the "cellular" region of the cartilage. The acellular layer typically extends from 0.02 mm to 1.0 mm from the delaminated surface of the cartilage.

The present invention will now be described in the context of several specific examples. These examples are not intended to be limiting, and also comprises any modifications or equivalents within the scope if the invention.

EXEMPLIFICATION

Example 1

In this example subjects having delaminated cartilage will be treated with either 1) a waterjet, 2) a suction device, 3) a cavitation device or, 4) an indentation device, as well as appropriate control conditions. The subjects may be suitable animal models or human patients participating in a clinical trial. Pigs and rabbits (Ebihara G, et al., Cartilage repair in transplanted scaffold-free chondrocyte sheets using a minipig model, Biomaterials. 2012 May; 33(15):3846-51. Epub 2012 Feb. 25), goats (Vasara A I, et al., Subchondral bone reaction associated with chondral defect and attempted cartilage repair in goats, Calcif Tissue Int. 2004 January; 74(1):107-14. Epub 2003 Oct. 20) and rats (Mogan, C., et al., Application of in vivo micro-computed tomography in the temporal characterisation of subchondral bone architecture in a rat model of low-dose monosodium iodoacetate-induced osteoarthritis, Arthritis Res Ther. 2011; 13(6):R210. Epub 2011 Dec. 21) are known in the art as being a suitable model system for the study of bone, cartilage and other joint-related diseases in humans, however, any mammalian model system known to one of ordinary skill in the art for studying the delamination of cartilage can be used.

The reattachment do the cartilage will be monitored by methods known to those of skill in the art. Such methods may include, for example, x-rays, magnetic imaging, ultrasound imaging, CT scanning, etc., of the treated area. Monitoring will take place as long as necessary to gather long term results. For example, monitoring may take place weekly for up to three months and then monthly or quarterly for up to five years or more. The results will show a statistically significant improvement of reattachment with test conditions 1)-4) as compared to control conditions. Long term monitoring of the subjects will take into account use of the joint by the subject or other location treated by the conditions noted above.

One of ordinary skill in the art will be able to develop other experiments to quantitate specific protocols used in the present invention as well as optimal times, pressures, repeat treatments, etc., and to determine a system of pretreatment that includes preparation of the bone surface and/or mechanical disruption using, for example, Pridie drilling, etc.

The invention claimed is:

1. A method for promoting the reattachment of a delaminated cartilage to a bone at a cartilage-bone interface, comprising:
   subjecting an acellular layer comprising avascular tissues at a site of the delaminated cartilage surface to a fluid movement generated by one or more of a positive pressure, a negative pressure or a cavitation or a combination thereof, wherein said fluid movement removes at least a portion of the acellular layer, thereby promoting the reattachment of said delaminated cartilage to said bone;
   wherein said promoting the reattachment of a delaminated cartilage to a bone at a cartilage bone interface does not involve perforation of subchondral bone to generate a blood clot.

2. The method of claim 1, wherein said fluid movement is produced by a water jet.

3. The method of claim 1, wherein said fluid movement is produced by a suction producing device.

4. The method of claim 1, wherein said fluid movement generated by said cavitation comprises contact of a liquid with an ultrasound transducer.

5. The method of claim 1, wherein said method further comprises a subchondral disruption of a bone surface.

6. The method of claim 5, wherein said subchondral disruption comprises at least partial removal of a calcified cartilage from a bone surface.

7. The method of claim 6, wherein said calcified cartilage is removed from about 0.02 mm to about 3.0 mm from the bone surface.

8. The method of claim 1, wherein said promoting the reattachment of the delaminated cartilage is controlled by regulating said positive or said negative pressure or both.

9. The method of claim 1, wherein said promoting the reattachment of the delaminated cartilage comprises promoting an inflammatory reaction.

10. The method of claim 1, wherein said method further comprises administering a biophysically compatible glue or an adhesive agent at an interface between the cartilage and the bone.

11. The method of claim 10, wherein said adhesive agent is a fibrin-based adhesive agent.

12. The method of claim 8, wherein said promoting the reattachment of the delaminated cartilage comprises removing from about 0.02 mm to about 1.0 mm of the cartilage.

13. The method of claim 11, wherein said promoting the reattachment of the delaminated cartilage comprises removing about 0.1 mm of the cartilage.

14. The method of claim 1, wherein said method further comprises exposing the acellular layer of the delaminated cartilage to a mechanical exfoliant.

15. The method of claim 14, wherein said mechanical exfoliants are granules.

16. The method of claim 14, wherein said mechanical exfoliants are selected from the group consisting of sodium tetraborate decahydrate granules, polyethylene silica, calcium carbonate, natural ground seeds, natural ground beans, aluminum oxide, monosaccharides, disaccharides and ice crystals.

17. The method of claim 1, wherein said method further comprises exposing the acellular layer of the delaminated cartilage to an exfoliant.

18. The method of claim 17, wherein said exfoliant is a chemical exfoliant.

19. The method of claim 18, wherein said chemical exfoliant is selected from the group consisting of alpha hydroxyl acid, beta hydroxyl acid, one or more citrus juices and papain.

* * * * *